(12) United States Patent
Zhu et al.

(10) Patent No.: US 8,370,087 B2
(45) Date of Patent: Feb. 5, 2013

(54) BICYCLE POWER METER WITH FRAME MOUNTED SENSOR

(75) Inventors: Shengbo Zhu, San Jose, CA (US); Su Shiong Huang, Bellevue, WA (US)

(73) Assignee: Silicon Valley Micro E Corporation, San Jose, CA (US)

( * ) Notice: Subject to any disclaimer, the term of this patent is extended or adjusted under 35 U.S.C. 154(b) by 467 days.

(21) Appl. No.: 12/583,099

(22) Filed: Aug. 15, 2009

(65) Prior Publication Data

US 2011/0040500 A1 Feb. 17, 2011

(51) Int. Cl.
*G01L 1/00* (2006.01)
(52) U.S. Cl. .......................................... 702/44
(58) Field of Classification Search ............... 702/44
See application file for complete search history.

(56) References Cited

U.S. PATENT DOCUMENTS

| | | | |
|---|---|---|---|
| 5,031,455 A | 7/1991 | Cline | |
| 5,992,553 A | 11/1999 | Morrison | |
| 6,418,797 B1 * | 7/2002 | Ambrosina et al. | 73/862.29 |
| 7,806,006 B2 * | 10/2010 | Phillips et al. | 73/862.338 |
| 8,011,242 B2 * | 9/2011 | O'Neill et al. | 73/379.01 |
| 2007/0245835 A1 | 10/2007 | Hauschildt | |

FOREIGN PATENT DOCUMENTS

GB 2321708 A 8/1998

OTHER PUBLICATIONS

Wikipedia article (authors unknown), "Cycling power meter", four pages.
Charles J. Murray, "Wireless Power Meters Help Olympic Athletes", www.designnews.com. three pages.
Author unknown, "Power: The Ultimate Training Metric", www.competitivecyclist.com, 25 pages.

* cited by examiner

*Primary Examiner* — Aditya Bhat

(57) ABSTRACT

A bicycle power meter has a strain gauge sensor assembly mounted on a relatively compressible portion of the end of the rear fork of the bicycle frame. The relatively compressible portion is near the rear hub and subject to the forces exerted by the cyclist to the crankset, and transferred via the chain, and sprocket assembly to the hub. The sensor assembly has two ohmically interconnected stretch sensors each having a first layer bearing a variable resistance element, whose resistance changes with displacement of the compressible portion, and a second layer for providing support for the first layer. The sensor assembly is connected in a bridge circuit to two other resistances to generate signals representative of cyclist applied force. These signals are processed along with velocity signals to generate power signals and the power signals are supplied to a display.

20 Claims, 10 Drawing Sheets

BICYCLE POWER METER WITH FRAME MOUNTED SENSOR

BACKGROUND OF THE INVENTION

This invention relates to bicycle power meters used to indicate the amount of power expended by the bicyclist during cycling. More particularly, this invention relates to a bicycle power meter using a frame mounted sensor for enabling the generation of electrical signals from which power can be determined.

Bicycle power meters are being increasingly used by both professional and amateur cyclists as an aid in developmental training. Several different types of bicycle power meters are available, some of which use strain gauges to measure the force applied by the cyclist to the crankset, the bottom bracket or the rear wheel hub. While effective in providing electrical signals representative of applied force, known bicycle power meters using strain gauges are relatively expensive and somewhat difficult to install. Due to these disadvantages, bicycle power meters have not found wide acceptance in the bicycling community.

SUMMARY OF THE INVENTION

The invention comprises a bicycle power meter using one or more strain gauge sensor assemblies, which is relatively inexpensive but effective in providing electrical signals representative of applied cyclist force, which signals can be combined with speed signals to generate real time power measurements.

In a broadest aspect, the invention comprises a bicycle power meter with a rear bicycle frame having a first fork with a relatively compressible rear portion adjacent a region to which a hub can be attached; and a strain gauge sensor assembly secured to the relatively compressible rear portion, the strain gauge sensor assembly having first and second stretch sensors each including a first layer having a variable resistance element mounted thereon and a second layer for supporting the first layer, the variable resistance elements of the first and second stretch sensors being ohmically interconnected to present a total resistance value representative of cyclist force.

The first and second stretch sensors are alternatively arranged with each first layer in facing relation, or with each second layer in facing relation.

The bicycle power meter further includes a bridge circuit having the first and second stretch sensors connected in a first branch and a pair of fixed resistances connected in a second branch; an amplifier coupled to the bridge circuit for amplifying signals representative of the total resistance value; an analog-to-digital converter coupled to the amplifier for converting the signals output from the amplifier to digital signals; a microcomputer coupled to the analog-to-digital converter for receiving the digital signals and bicycle velocity signals from an associated bicycle speedometer and converting the received signals to power signals; and a display coupled to the microcomputer for displaying the power signals to a cyclist.

The bicycle power meter can be configured as either a wired or a wireless system. In a wired system, the units are all ohmically interconnected. In a wireless system, a transmitter is coupled to the microcomputer for receiving the power signals and generating equivalent wireless signals; and a receiver coupled to the display receives the equivalent wireless signals and provides the equivalent wireless signals to the display.

In an alternative embodiment, the rear bicycle frame has a second fork with a second relatively compressible rear portion adjacent a region to which a hub can be attached; and an additional strain gauge sensor assembly is secured to the second relatively compressible rear portion. The additional strain gauge sensor assembly has third and fourth stretch sensors each including a first layer having a variable resistance element mounted thereon and a second layer for supporting the first layer, the variable resistance elements of the third and fourth stretch sensors being ohmically interconnected to present a total resistance value representative of cyclist force.

The third and fourth stretch sensors are alternatively arranged with each first layer in facing relation, or with each second layer in facing relation.

In this alternative embodiment, the third and fourth stretch sensors are connected in the second branch of the bridge circuit.

The invention greatly facilitates the inclusion of a bicycle power meter with any bicycle having a relatively compressible structural portion at the end of the rear fork of the bicycle frame. The entire power meter system, or just the strain gauge sensor assemblies, can be easily secured to the bicycle components at the point of manufacture. Similarly, the entire system can be readily secured to the bicycle at any point in the distribution chain, such as at the retailer as an add-on option. The bicyclist can also add the bicycle power meter system to a bicycle after purchase, at relatively low cost and effort.

For a fuller understanding of the nature and advantages of the invention, reference should be made to the ensuing detailed description taken in conjunction with the accompanying drawings.

DETAILED DESCRIPTION OF THE PREFERRED EMBODIMENTS

Figure 1:
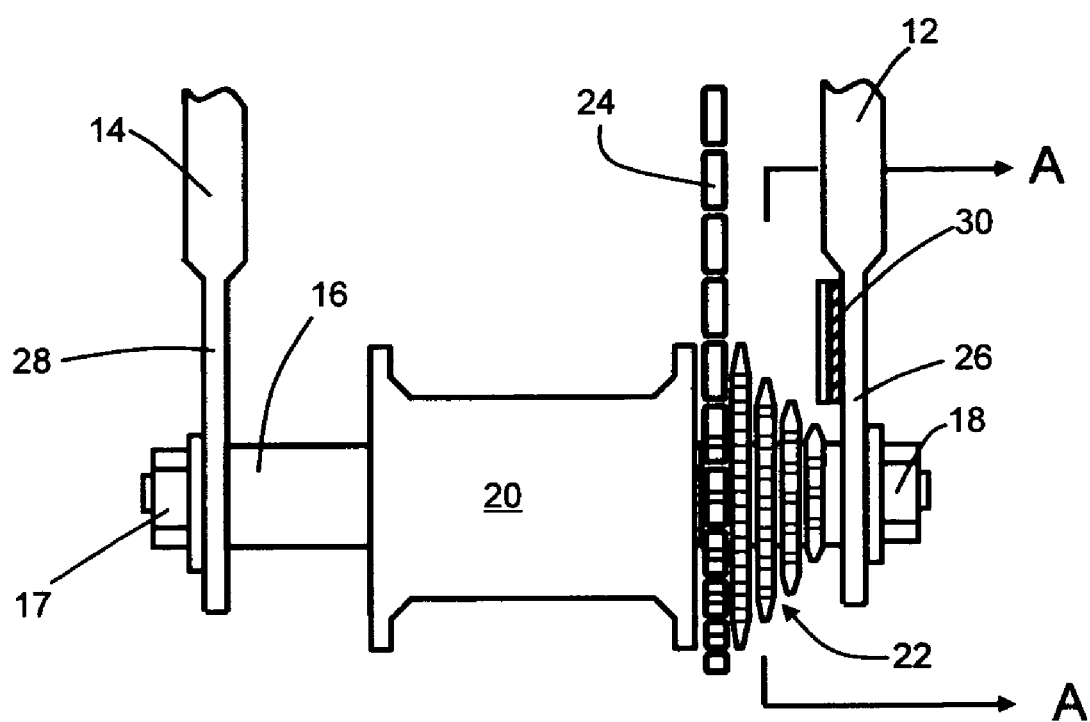
FIG. 1 is a perspective partial view taken from above of a bicycle rear frame illustrating the fork ends, hub, chain and strain gauge sensor assembly of a first embodiment of the invention.

Turning now to the drawings, FIG. 1 is a perspective partial view taken from above of a bicycle rear frame illustrating the fork ends, hub, chain and strain gauge sensor assembly of a first embodiment of the invention. As seen in this Fig., a bicycle rear frame has a pair of terminating portions termed a right fork 12 and a left fork 14. Secured between forks 12, 14 by means of an axle 16 and capture nuts 17, 18 are a rear hub 20 and a sprocket assembly 22. A drive chain 24 passes around individual sprockets comprising sprocket assembly 22 in order to provide rotational movement of hub 20 is response to cycling effort by the cyclist.

Figure 2:
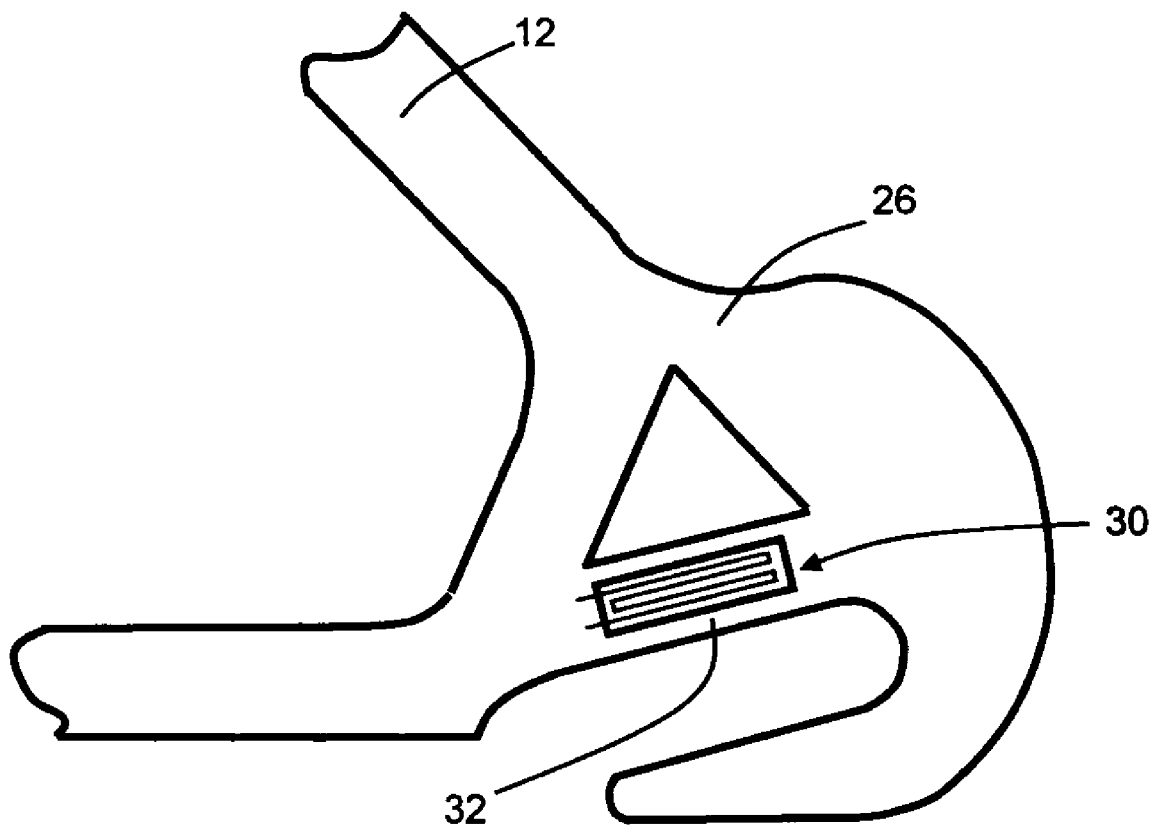
FIG. 2 is an elevational view taken along lines A-A of FIG. 1 illustrating the mounting position of the strain gauge sensor assembly on the inner surface of a compressible portion of the right rear fork.

The end portion 26, 28 of each of forks 12, 14 has a thinner lateral thickness dimension than the remaining major portion of each fork 12, 14. Secured to the inner surface of end portion 26 of right fork 12 is a strain gauge sensor assembly 30 described more fully below. As best shown in FIG. 2, strain gauge sensor assembly 30 is attached to a thin web portion 32 extending along end portion 26 of right fork 12. Web portion 32 has the mechanical property of being relatively compressible when compared to the more robust structure of right rear fork 12, so that the physical dimensions of strain gauge sensor assembly 30 can change with different force magnitudes applied to web portion 32 via chain 24, sprocket assembly 22, and axle 16.

Figure 5:
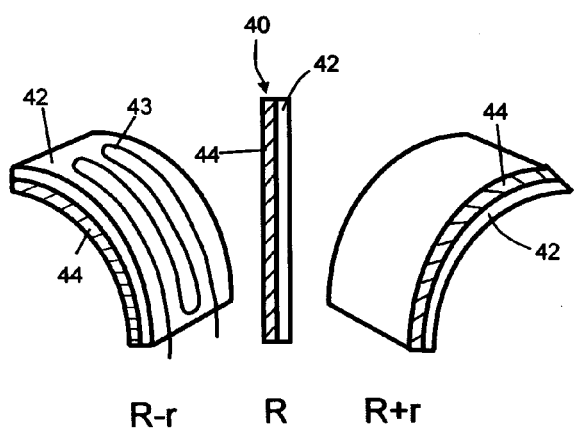
FIG. 5 is a schematic view of a single strain gauge sensor illustrating the sensor in three different positions.

FIG. 5 illustrates a simple stretch sensor 40 having the property of an ohmic resistance which varies in a predictable amount with linear longitudinal displacement of the sensor body. Stretch sensor 40 has a first layer 42 on which a thin variable resistance element 43 is mounted, and a second base layer 44 which carries the first layer and provides additional mechanical strength for sensor 40. The resistance value of sensor 40 depends upon the longitudinal displacement of the sensor body. As shown in FIG. 5, when sensor 40 is displaced in one direction (illustrated as flexing) in a first direction, the value of the resistance increases (R+r), where R is the at rest resistance value of sensor 40 and r is the additional resistance value due to the displacement in the first direction. Similarly, when sensor 40 is displaced in the opposite direction, the value of the resistance decreases (R−r).

Figure 6:
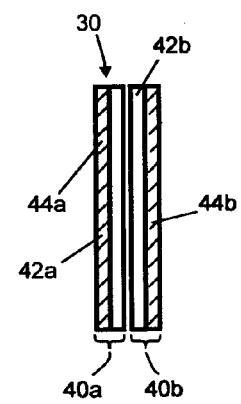
FIG. 6 is a schematic view of a first embodiment of a dual element strain gauge sensor assembly.

FIG. 6 illustrates a strain gauge sensor assembly 30 of the type incorporated into the power meter configuration shown in FIGS. 1 and 2. As seen in this Fig., sensor assembly 30 comprises two two layer stretch sensors 40a, 40b having first layers 42a, 42b, and second layers 44a, 44b. Stretch sensors 40a, 40b are arranged with the first layers 42a, 42b in facing relation in an (R+r), (R−r) relation. As sensor assembly 30 is displaced by forces applied to web portion 32 of right rear fork 12, the total resistance of each stretch sensor will vary in equal and opposite directions.

Figure 7:
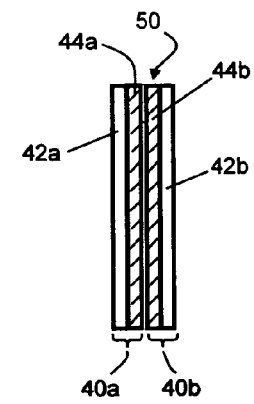
FIG. 7 is a schematic view of a second embodiment of a dual element strain gauge sensor assembly.

FIG. 7 illustrates an alternate strain gauge sensor assembly 50 of the type incorporated into the power meter configuration shown in FIGS. 1 and 2. As seen in this Fig., sensor assembly 50 comprises two two layer stretch sensors 40a, 40b having first layers 42a, 42b, and second layers 44a, 44b. Stretch sensors 40a, 40b are arranged with the second layers 44a, 44b in facing relation in an (R−r), (R+r) relation. As sensor assembly 50 is displaced by forces applied to web portion 32 of right rear fork 12, the total resistance of each stretch sensor will vary in equal and opposite directions.

Figure 3:
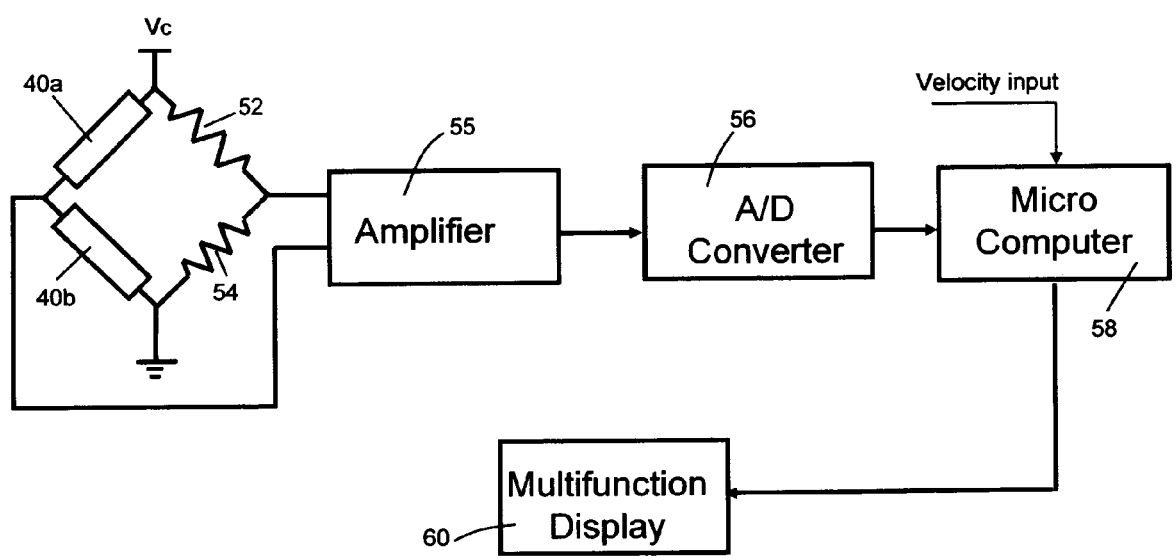
FIG. 3 is a block diagram of a bicycle power meter unit using a single strain gauge sensor assembly configured as a wired unit.

FIG. 3 is a block diagram of a bicycle power meter unit using a single strain gauge sensor assembly configured as a wired unit. As seen in this Fig., the stretch sensors 40a, 40b comprising strain gauge sensor assembly 30 or 50 are connected to a pair of fixed resistances 52, 54 in a well-known Wheatstone bridge circuit configuration. The top node of the bridge is connected to a source of electrical potential Vc supplied by a battery. The bottom node of the bridge is connected to circuit ground. The right node is connected to one end of the fixed resistances 52, 54 and serves as one output terminal of the bridge circuit. The second end of fixed resistance 52 is connected to one end of stretch sensor 40a and to supply voltage Vc. The second end of fixed resistance 54 is connected to one end of stretch sensor 40b and to circuit ground. The other ends of stretch sensors 40a, 40b are connected together and serve as the other output terminal of the bridge circuit.

The bridge circuit output terminals are coupled to the input terminals of an amplifier 55, where the bridge signals are amplified. Amplifier 55 is preferably a type MAX4197 unit available from MAXIM Corporation. The amplified signals output from amplifier 55 are coupled to the input of an analog-to-digital converter 56 which converts the amplified analog signals to digital equivalent signals. The digital signals output from analog-to-digital converter 56 are coupled to an input port of a microcomputer 58. Analog-to-digital converter 56 and microcomputer 58 are preferably combined in a type PIC 16F73 unit available from Microchip Corporation. Velocity signals from a bicycle speedmeter (not shown) are also coupled to microcomputer 58. Microcomputer 58 processes the force signals and the velocity signals using a known algorithm to provide power magnitude signals. The power magnitude signals are coupled to a multifunction display 60, which displays the current power value in readable form by the bicyclist. In the FIG. 3 embodiment the units are coupled together by ohmic wire connections.

Figure 4:
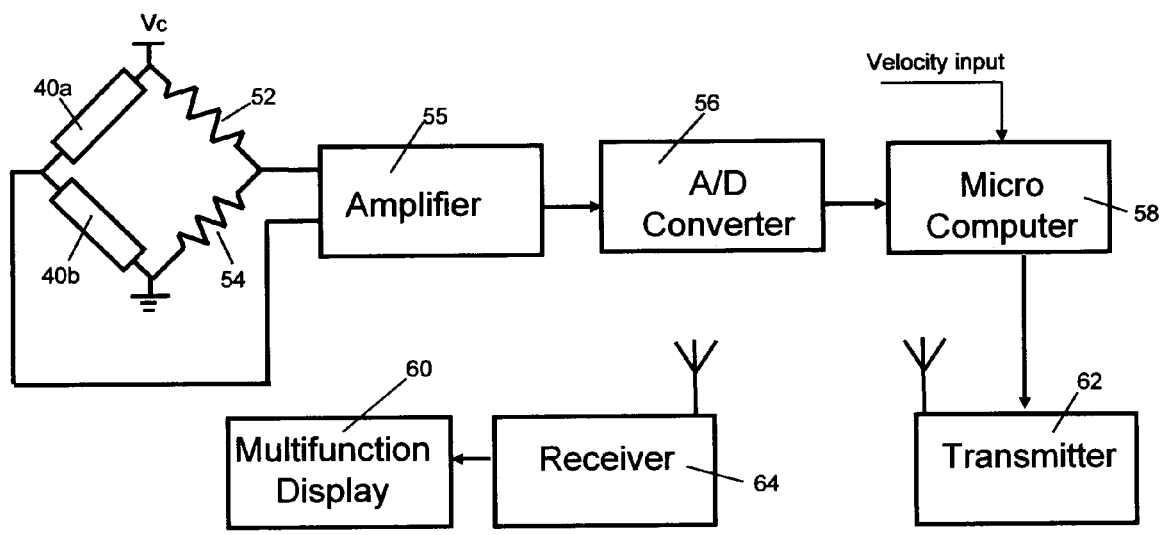
FIG. 4 is a block diagram of a bicycle power meter unit using a single strain gauge sensor assembly configured as a wireless unit.

FIG. 4 is a block diagram of a bicycle power meter unit using a single strain gauge sensor assembly configured as a wireless unit. In this Fig., elements corresponding to the same elements in the system of FIG. 3 are designated with the same reference numerals. In the FIG. 4 system, the processed power signals are coupled to the input of an r.f transmitter 62 located near the sensor assembly 30 (50). Transmitter 62 transmits the power signals to a receiver 64 located near the multifunction display 60, which supplies these signals to the multifunction display 60.

Figure 8:
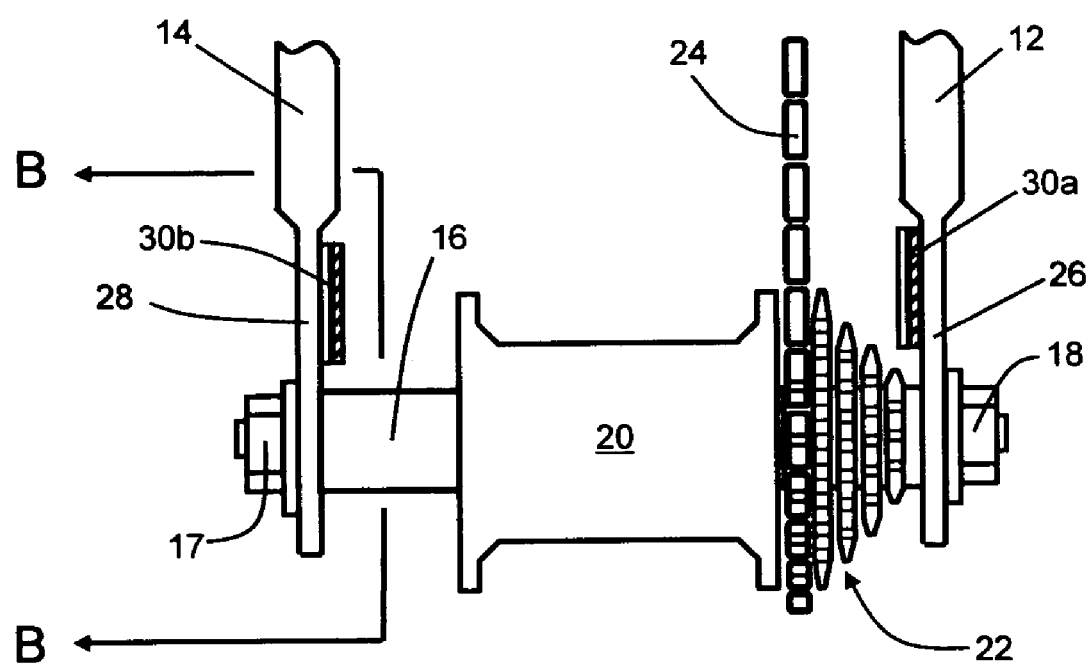
FIG. 8 is a perspective partial view taken from above of a bicycle rear frame illustrating the fork ends, hub, chain and strain gauge sensor assembly of a second embodiment of the invention having two separate strain gauge sensor assemblies.
Figure 9:
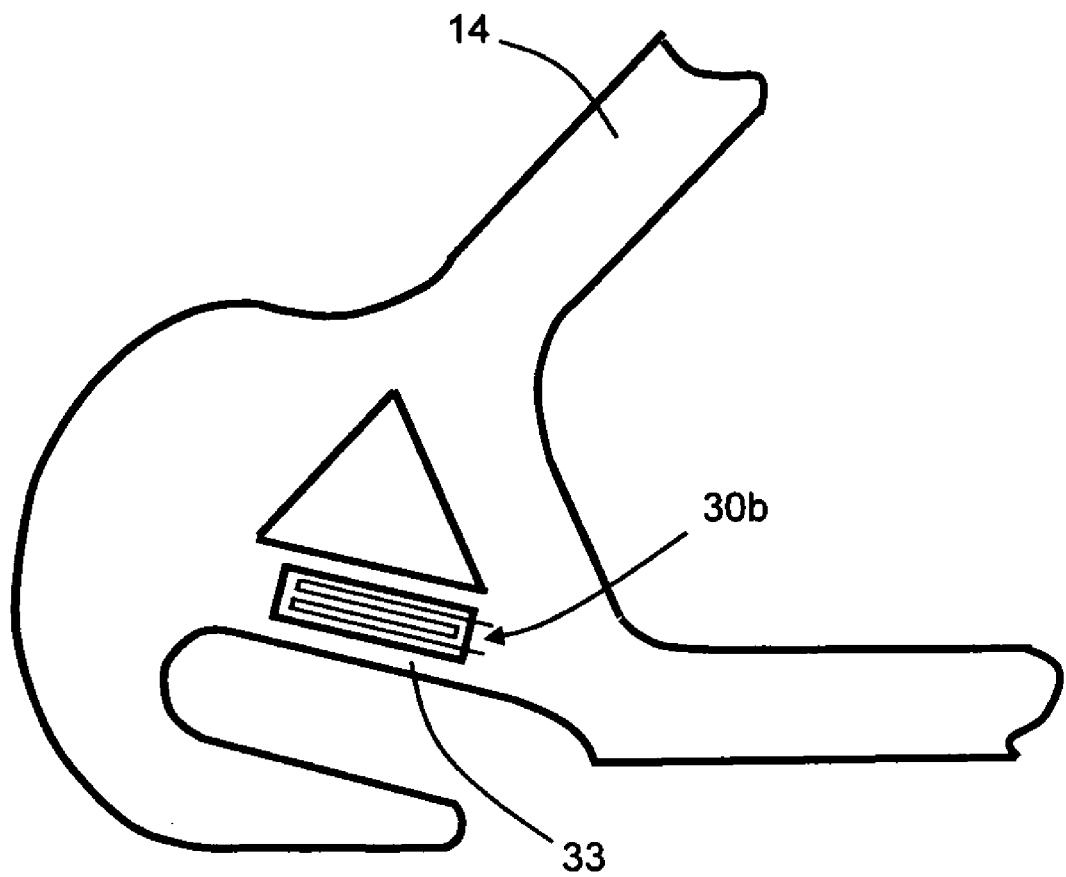
FIG. 9 is an elevational view taken along lines B-B of FIG. 8 illustrating the mounting position of the second strain gauge sensor assembly on the inner surface of a compressible portion of the left rear fork.

FIG. 8 is a perspective partial view taken from above of a bicycle rear frame illustrating the fork ends, hub, chain and strain gauge sensor assembly of a second embodiment of the invention having two separate strain gauge sensor assemblies. In this Fig., elements corresponding to the same elements shown in FIG. 1 are designated with the same reference numerals, with the exception of sensor assembly 30 which is designated with reference 30a. Secured to the inner surface of end portion 28 of left fork 14 is a second strain gauge sensor assembly 30b. Sensor assembly 30b has the same structure and function as sensor assembly 30 described above. As best shown in FIG. 9, strain gauge sensor assembly 30b is attached to a thin web portion 33 extending along end portion 28 of left fork 14. Web portion 33 has the mechanical property of being relatively compressible when compared to the more robust structure of left rear fork 14, so that the physical dimensions of strain gauge sensor assembly 30b can change with different force magnitudes applied to web portion 33 via chain 24, sprocket assembly 22, and axle 16.

Figure 10:
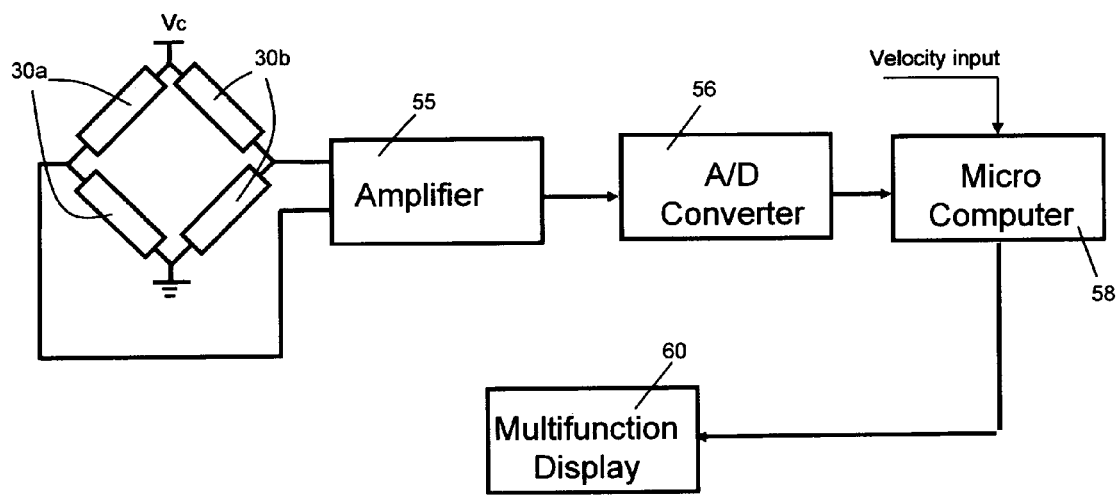
FIG. 10 is a block diagram of a bicycle power meter unit using two strain gauge sensor assemblies configured as a wired unit.
Figure 11:
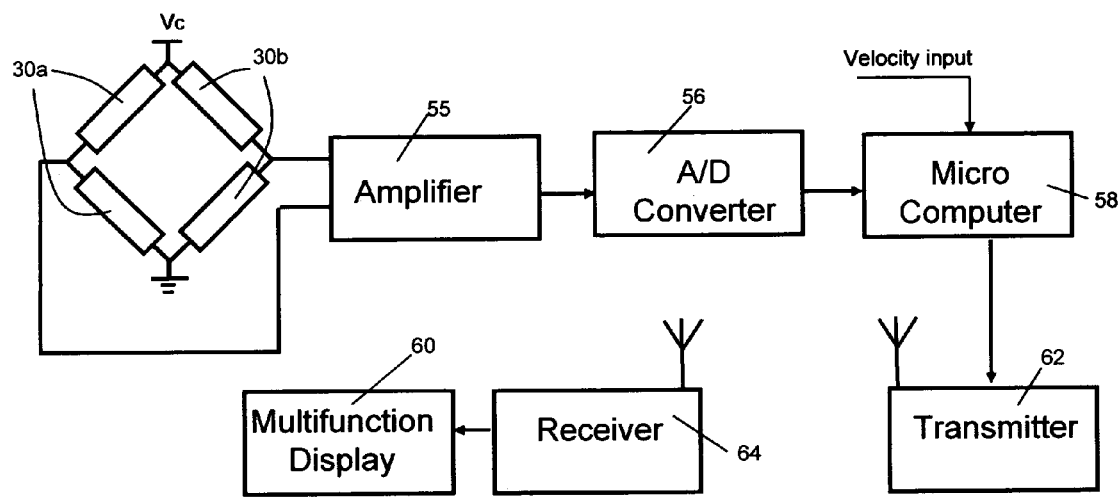
FIG. 11 is a block diagram of a bicycle power meter unit using two strain gauge sensor assemblies configured as a wireless unit.

FIG. 10 is a block diagram of a bicycle power meter unit using two strain gauge sensor assemblies 30a, 30b configured as a wired unit. FIG. 11 is a block diagram of a bicycle power meter unit using two strain gauge sensor assemblies 30a, 30b configured as a wireless unit. The principal elements shown in each Fig. are essentially the same as those shown in FIGS. 3 and 4, with the exception of the configuration of the bridge circuit. In both FIGS. 10 and 11, the fixed resistances 52, 54 are replaced by the individual stretch sensors 40a, 40b comprising the second sensor assembly 30b, with electrical connections as shown. Thus, the bridge comprises four individual variable resistance stretch sensors 40.

Figure 12:
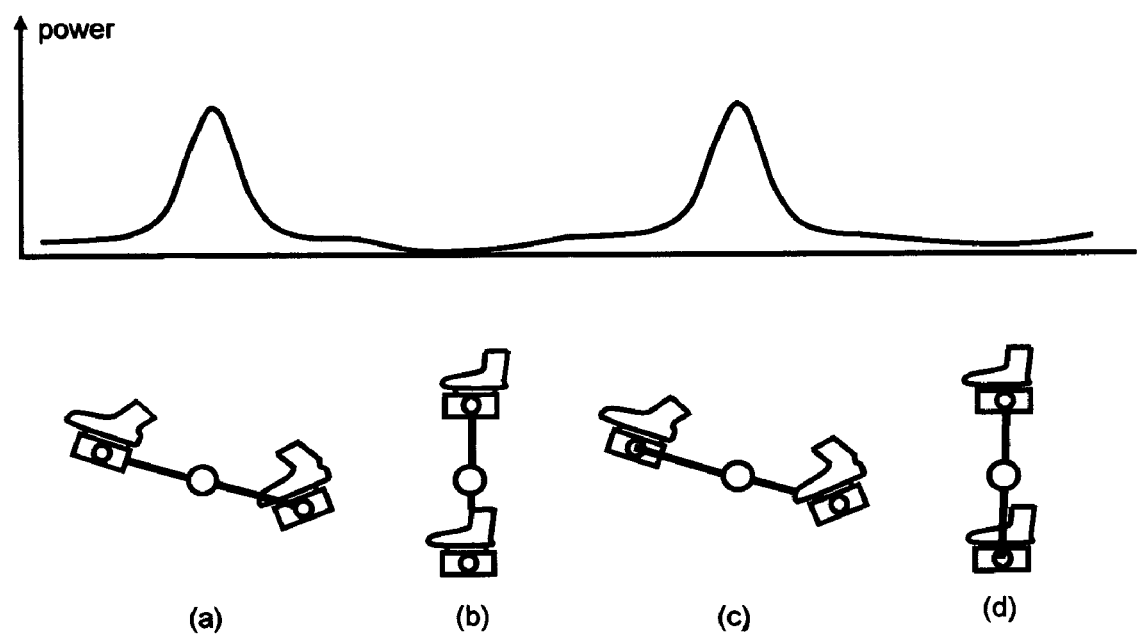
FIG. 12 is a schematic diagram illustrating variation in cyclist power with crankset angular position.

In use, as the cyclist applies force to the bicycle pedals, the magnitude of the force is monitored by the bridge circuit and converted to visible power display signals for the bicyclist to observe. FIG. 12 is a schematic diagram illustrating variation in cyclist power with crankset angular position. In position (a) the pedals are essentially horizontal and the cyclist is applying maximum force with the forward pedal. In position (b) the pedals are essentially vertical and the cyclist is applying minimum force. In position (c) the pedals are again essentially horizontal and the cyclist is applying maximum force with the forward pedal; while in position (d) the pedals are again essentially vertical and the cyclist is applying minimum force.

As will now be apparent, bicycle power meters fabricated according to the teachings of the invention offer cost and ease of installation advantages over known bicycle power meters using strain gauges. Firstly, the strain gauges are relatively simple to install on any bicycle frame having the relatively compressible thin web portion adjacent the rear hub. This installation can be done at the bicycle factory or elsewhere in the chain of commerce (e.g., by the retailer or the user-bicyclist). In addition, bicycle power meters fabricated according to the teachings of the invention can be configured in either a wired or a wireless mode, which affords great flexibility in the installation process. Further, by employing the two layer dual strain gauge assemblies, greater sensitivity is achieved over single strain gauge designs. Lastly, by employing the four strain gauge configuration shown in FIGS. 8-11, a high level of insensitivity to temperature variations encountered during cycling can be achieved.

While the invention has been described with reference to particular embodiments, various modifications, alternate constructions and equivalents may be employed without departing from the spirit of the invention. For example, while certain circuit components have been disclosed, other equivalent units may be employed, as desired. Therefore, the above should not be construed as limiting the invention, which is defined by the appended claims.

What is claimed is:

1. A bicycle power meter comprising:
a rear bicycle frame having a first fork with a main body portion and an end portion adjacent a region to which a hub can be attached, said end portion having a thinner thickness dimension than said main body portion and being relatively more compressible than said main body portion; and
a strain gauge sensor assembly having first and second stretch sensors each including a first layer having a variable resistance element mounted thereon and a second layer for supporting said first layer, one of said first and second stretch sensors being fixedly attached to said relatively more compressible end portion of said first fork, the variable resistance elements of said first and second stretch sensors being ohmically interconnected to present a total resistance value representative of cyclist force at said end portion.

2. The invention of claim 1 wherein said first and second stretch sensors are arranged with each said first layer in facing relation.

3. The invention of claim 1 wherein said first and second stretch sensors are arranged with each said second layer in facing relation.

4. The invention of claim 1 further including a bridge circuit having said first and second stretch sensors connected in a first branch and a pair of fixed resistances connected in a second branch; an amplifier coupled to said bridge circuit for amplifying signals representative of said total resistance value; an analog-to-digital converter coupled to said amplifier for converting the signals output from said amplifier to digital signals; a microcomputer coupled to said analog-to-digital converter for receiving said digital signals and bicycle velocity signals from an associated bicycle speedometer and converting the received signals to power signals; and a display coupled to said microcomputer for displaying the power signals to a cyclist.

5. The invention of claim 4 further including a transmitter coupled to said microcomputer for receiving said power signals and generating equivalent wireless signals; and a receiver having an output coupled to said display for receiving said equivalent wireless signals and providing said equivalent wireless signals to said display.

6. The invention of claim 1 wherein said rear bicycle frame has a second fork with a main body portion and an end portion adjacent a region to which a hub can be attached, said end portion of said second fork having a thinner thickness dimension than said main body portion of said second fork and being relatively more compressible than said main body portion of said second fork; and an additional strain gauge sensor assembly having third and fourth stretch sensors each including a first layer having a variable resistance element mounted thereon and a second layer for supporting said first layer, one of said third and fourth stretch sensors being fixedly attached to said relatively more compressible end portion of said second fork, the variable resistance elements of said third and fourth stretch sensors being ohmically interconnected to present a total resistance value representative of cyclist force at said end portion of said second fork.

7. The invention of claim 6 wherein said third and fourth stretch sensors are arranged with each said first layer in facing relation.

8. The invention of claim 6 wherein said third and fourth stretch sensors are arranged with each said second layer in facing relation.

9. The invention of claim 6 further including a bridge circuit having said first and second stretch sensors connected in a first branch and said third and fourth stretch sensors connected in a second branch; an amplifier coupled to said bridge circuit for amplifying signals representative of said total resistance value; an analog-to-digital converter coupled to said amplifier for converting the signals output from said amplifier to digital signals; a microcomputer coupled to said analog-to-digital converter for receiving said digital signals and bicycle velocity signals from an associated bicycle speedometer and converting the received signals to power signals; and a display coupled to said microcomputer for displaying the power signals to a cyclist.

10. The invention of claim 9 further including a transmitter coupled to said microcomputer for receiving said power signals and generating equivalent wireless signals; and a receiver having an output coupled to said display for receiving said equivalent wireless signals and providing said equivalent wireless signals to said display.

11. The invention of claim 6 wherein said end portion of said second fork includes a web portion; and wherein said additional strain gauge sensor assembly is secured to said web portion of said end portion of said second fork.

12. The invention of claim 1 wherein said end portion includes a web portion; and wherein said strain gauge sensor assembly is secured to said web portion.

13. A bicycle power meter comprising:
- a rear bicycle frame having a first fork with a main body portion and an end portion adjacent a region to which a hub can be attached, said end portion having a thinner thickness dimension than said main body portion and being relatively more compressible than said main body portion;
- a strain gauge sensor assembly having first and second stretch sensors each including a first layer having a variable resistance element mounted thereon and a second layer for supporting said first layer, one of said first and second stretch sensors being fixedly attached to said relatively more compressible end portion of said first fork, the variable resistance elements of said first and second stretch sensors being ohmically interconnected to present a total resistance value representative of cyclist force at said end portion;
- a bridge circuit having said first and second stretch sensors connected in a first branch and a pair of resistances connected in a second branch;
- an amplifier coupled to said bridge circuit for amplifying signals representative of said total resistance value;
- an analog-to-digital converter coupled to said amplifier for converting the signals output from said amplifier to digital signals;
- a microcomputer coupled to said analog-to-digital converter for receiving said digital signals and bicycle velocity signals from an associated bicycle speedometer and converting the received signals to power signals; and
- a display coupled to said microcomputer for displaying the power signals to a cyclist.

14. The invention of claim 13 wherein said first and second stretch sensors are arranged with each said first layer in facing relation.

15. The invention of claim 13 wherein said first and second stretch sensors are arranged with each said second layer in facing relation.

16. The invention of claim 13 further including a transmitter coupled to said microcomputer for receiving said power signals and generating equivalent wireless signals; and a receiver having an output coupled to said display for receiving said equivalent wireless signals and providing said equivalent wireless signals to said display.

17. The invention of claim 13 wherein said rear bicycle frame has a second fork with a main body portion and an end portion adjacent a region to which a hub can be attached, said end portion of said second fork having a thinner thickness dimension than said main body portion of said second fork and being relatively more compressible than said main body portion of said second fork; and an additional strain gauge sensor assembly having third and fourth stretch sensors each including a first layer having a variable resistance element mounted thereon and a second layer for supporting said first layer, one of said third and fourth stretch sensors being fixedly attached to said relatively more compressible end portion of said second fork, the variable resistance elements of said third and fourth stretch sensors being ohmically interconnected to present a total resistance value representative of cyclist force at said end portion of said second fork and comprising said pair of resistances in said bridge circuit.

18. The invention of claim 17 wherein said third and fourth stretch sensors are arranged with each said first layer in facing relation.

19. The invention of claim 17 wherein said third and fourth stretch sensors are arranged with each said second layer in facing relation.

20. The invention of claim 13 wherein said end portion includes a web portion; and wherein said strain gauge sensor assembly is secured to said web portion.

* * * * *